United States Patent [19]

Anilionis et al.

[11] Patent Number: 4,952,682
[45] Date of Patent: Aug. 28, 1990

[54] EFFICIENT PROKARYOTIC EXPRESSION SYSTEM

[75] Inventors: Algis Anilionis; John L. Palmer, both of Arlington, Mass.

[73] Assignee: Repligen Corporation, Cambridge, Mass.

[21] Appl. No.: 253,351

[22] Filed: Sep. 30, 1988

Related U.S. Application Data

[60] Continuation of Ser. No. 109,003, Oct. 16, 1987, abandoned, which is a division of Ser. No. 686,344, Dec. 26, 1984, Pat. No. 4,721,671.

[51] Int. Cl.$^5$ .................... C07K 13/00; C12P 21/00; C12N 15/00
[52] U.S. Cl. .................... 530/350; 435/69.7; 435/69.8; 435/172.3; 435/320; 935/47; 935/48; 935/73
[58] Field of Search ............. 530/350; 435/69.7, 69.8, 435/172.3, 320; 935/47, 48, 73

[56] References Cited

U.S. PATENT DOCUMENTS 4,356,270 10/1982 Itakura .................. 435/317

OTHER PUBLICATIONS

Hieber. *Biochem. and Biophys. Res. Comm.* 104(4):1271–1278, 1982.
Blanco. *J. Bacteriol.* 149:587–594, 1982.
Ritzenthaler. *Mol. Gen. Genet.* 191:263–270, 1983.
Ashwell. *Meth. in Enzymol.* 5:190–208, 1962.

Primary Examiner—Thomas D. Mays
Attorney, Agent, or Firm—Saliwanchik & Saliwanchik

[57] ABSTRACT

A novel highly effective prokaryotic expression system is exemplified specifically by being used to produce the useful enzyme $\beta$-glucuronidase (BG). This system uses a hybrid plasmid comprising BG gene promoter DNA. The level of expression of BG by an *E. coli* K-12 derivative host is in the 50% of total cellular protein range. The invention expression system also can be used to express other useful proteins, as disclosed herein.

1 Claim, 3 Drawing Sheets

```
        Sau3A                           Taq I
          GATCTGACCT ACGGTGTACT GGCCGATATC GAAGCGGAAG ACCTGGCGCG

TGAAGCGTCG TTTGCTCAGG GATTACGCGC GATGATTGGC GGTATCTTAA CCGCATCCTG

ATTCTCTCTC TTTTTCGGCG GGCTGGTGAT AACTGTGCCC GCGTTTCATA TCGTAATTTC

EcoRI
TCTGTGCAAA AATTATCCTT CCCGGCTTCG GAGAATTCCC CCCAAAATAT TCACTGTAGC
NdeI                                    Taq I
CATATGTCAT GAGAGTTTAT CGTTCCCAAT ACGCTCGAAC GAACGTTCGG TTGCTTATTT

AhaIII           Sau3A
TATGGCTTCT GTCAACGCTG TTTTAAAGAT TAATGCGATC TATATCACGC TGTGGGTATT

Sau3A                                            NcoI
GCAGTTTTTG GTTTTTTGAT CGCGGTGTCA GTTCTTTTTA TTTCCATTTC TCTTCCATGG

-------------------+---------------          HpaI
GTTTCTCACA GATAACTGTG TGCAACACAG AATTGGTTAA CTAATCAGAT TAAAGGTTGA
-------------------+---------------

RBS           1
CCAGTATTAT TATCTTAATG AGGAGTCCCT T ATG TTA CGT CCT GTA GAA ACC CCA
                                  MET LEU ARG PRO VAL GLU THR PRO

10                Taq I                  20        Sau3A
ACC CGT GAA ATC AAA AAA CTC GAC GGC CTG TGG GCA TTC AGT CTG GAT CGC
THR ARG GLU ILE LYS LYS LEU ASP GLY LEU TRP ALA PHE SER LEU ASP ARG

BclI
           30       Sau3A                                40
GAA AAC TGT GGA ATT GAT CAG CGT TGG TGG GAA AGC GCG TTA CAA GAA AGC
GLU ASN CYS GLY ILE ASP GLN ARG TRP TRP GLU SER ALA LEU GLN GLU SER

50        Sau3A
CGG GCA ATT GCT GTG CCA GGC AGT TTT AAC GAT CAG TTC GCC GAT GCA GAT
ARG ALA ILE ALA VAL PRO GLY SER PHE ASN ASP GLN PHE ALA ASP ALA ASP
```

Figure 2 (continued)

```
     60                                              70
ATT CGT AAT TAT GCG GGC AAC GTC TGG TAT CAG CGC GAA GTC TTT ATA CCG
ILE ARG ASN TYR ALA GLY ASN VAL TRP TYR GLN ARG GLU VAL PHE ILE PRO

80                              Taq I   90
AAA GGT TGG GCA GGC CAG CGT ATC GTG CTG CGT TTC GAT GCG GTC ACT CAT
LYS GLY TRP ALA GLY GLN ARG ILE VAL LEU ARG PHE ASP ALA VAL THR HIS 100                                     110
TAC GGC AAA GTG TGG GTC AAT AAT CAG GAA GTG ATG GAG CAT CAG GGC GGC
TYR GLY LYS VAL TRP VAL ASN ASN GLN GLU VAL MET GLU HIS GLN GLY GLY

120
TAT ACG CCA TTT GAA GCC GAT GTC ACG CCG TAT GTT ATT GCC GGG AAA AGT
TYR THR PRO PHE GLU ALA ASP VAL THR PRO TYR VAL ILE ALA GLY LYS SER

Rsa I   130                                             140
GTA CGT ATC ACC GTT TGT GTG AAC AAC GAA CTG AAC TGG CAG ACT ATC CCG
VAL ARG ILE THR VAL CYS VAL ASN ASN GLU LEU ASN TRP GLN THR ILE PRO 150                                     160
CCG GGA ATG GTG ATT ACC GAC GAA AAC GGC AAG AAA AAG CAG TCT TAC TTC
PRO GLY MET VAL ILE THR ASP GLU ASN GLY LYS LYS LYS GLN SER TYR PHE

BamHI
                                Sau3A
CAT GAT TTC TTT AAC TAT GCC GGG ATC
HIS ASP PHE PHE ASN TYR ALA GLY ILE
```

EFFICIENT PROKARYOTIC EXPRESSION SYSTEM

This application is a continuation, of application Ser. No. 109,003, filed Oct. 16, 1987 no abandoned, which is a division of application Ser. No. 686,344 filed Dec. 26, 1984, now U.S. Pat. No. 4,721,671.

BACKGROUND OF THE INVENTION

Expression of cloned DNA in bacteria has been extensively studied. Most available information concerns expression of cloned native, foreign, and hybrid genes in *E. coli* using portable promoters in plasmids, phage or cosmid cloning vectors. Recently several laboratories have reported expression levels of 30% of total cellular protein as a single protein product.

The *E. coli* gene uidA encodes the enzyme β-D-glucuronidase (E.C. 3.2.1.31) which is the first enzyme of the hexuronide-hexuronate pathway (Ashwell, G. [1962] Methods in Enzymol. 5:190-208). The enzyme is induced by β-D-glucuronides but hydrolyzes both β-D-glucuronides and the non-inducing β-D-galacturonides to their respective uronic acids. Subsequent enzymes of the pathway convert glucuronate or galacturonate to 2-keto-3-deoxy-gluconate (KDG), which is in turn fed into the glycolytic pathway after phosphorylation to produce KDG-6-P and conversion to pyruvate plus glyceraldehyde-3-phosphate.

The uidA gene has been shown to be under negative regulation by the closely linked upstream repressor gene uidR and also under partial or weaker negative control by the uxuR gene (Ritzenthaler, P., Blanco, C. and Mata-Gilsinger, M. [1983] Mol. Gen. Genet. 191: 263-270). uxuR is the repressor of the uxu operon which oroduces the enzymes necessary for the conversion of fructuronate to KGD later in the same pathway (Novel, M. and Novel, G. [1976] J. Bacteriol. 127:407-417; ibid, 418-432).

Blanco et al. (1982, J. Bact. 149:587-594) identified a plasmid Ul, from the *E. coli*-ColEl hybrid clone bank of Clarke and Carbon (1976, Cell 9:91-99), which carries the manA, uidA, uidR region of the *E. coli* chromosome. When fully induced, strain JA200(Ul) produced only 1.8-fold the β-D-glucuronidase enzyme induced in JA200. In contrast, subclones which carried the uidA gene without a uidR repressor gene copy produced sufficient enzyme to be visualized by Coomassie blue staining of a non-denaturing polyacrylamide gel (FIG. 3 in Blanco et al.).

BRIEF SUMMARY OF THE INVENTION

The subject invention concerns a newly recognized, highly efficient expression system which enables workers skilled in the art to achieve heretofore unattained levels of expression of cloned gene products, i.e., over 50% of total cellular protein of the bacterial host comprising a single polypeptide product. The expression system is exemplified herein to produce high yields of the useful enzyme β-glucuronidase (BG). This expression of high amounts of BG is achieved by use of a hybrid plasmid vector comprising *E. coli* BG gene DNA. It is surprising that the *E. coli* host transformed with the novel hybrid plasmid of the subject invention expresses BG in extremely high amounts in view of the known facts that BG is expressed in minute amounts by its native *E. coli* host, and that the known *E. coli* clones of the BG gene described by Blanco et al. (1982) do not express the BG enzyme at these ultrahigh levels. It is believed that this prior art level of expression of BG by *E. coli* has led persons skilled in the art away from using BG promoter DNA in prokaryotic expression systems. Rather, the well-characterized lac and trp promoters have been extensively used in prokaryotic expression systems.

Expression vectors which exemplify the subject high expression system invention are hybrid plasmids pBG101-41 and pBGl. Novel hybrid plasmid pBG101-41 contains approximately 6 kb of *E. coli* BG DNA inserted at the BamHI site of pBR322. Novel hybrid plasmid pBGl contains the 1237 base pair SalI-BamHI fragment of pBG101-41 ligated into a SalI. Bam HI cut pBR322 vector. Plasmid pBGl carries all the nucleotide bases necessary to achieve the high level expression of a host transformed with plasmid pBG101-41. See FIG. 2

DETAILED DISCLOSURE OF THE INVENTION

The subject invention, which is in the field of molecular biology, concerns expression vectors useful to produce the useful enzyme β-D-glucuronidase in a highly efficient manner. The level of expression of β-D-glucuronidase by a suitable *E. coli* host is at least 50% of total cellular protein.

β-D-glucuronidase is a useful biological tool. For example, it can be used in the determination of urinary steroids and of steroid conjugates in blood. The current high cost of this enz)nne is due to its minute presence in native *E. coli*. This invention greatly decreases the cost of production of this enzyme as the enzyme is produced at a level of 50% of total protein in the cell culture. This increase in expression level impacts cost of protein production in two independent and significant ways. Increased expression greatly increases the amount of the useful enzyme that can be produced in a growth vessel, for example a fermenter, of any given size. In addition, an increase in expression level greatly decreases the degree of difficulty encountered in the purification of the enzyme. In many of the applications of this useful protein it must be in pure form.

The expression system of the subject invention can be used to express other useful proteins as well as β-glucuronidase. These proteins can be expressed at high level either by inserting their gene behind the BG promoter or by making a hybrid gene which contains the BG promoter and the N-terminal sequences of the BG gene fused to coding sequences of the other gene. Useful proteins which can be expressed at elevated levels by one or both of these methods include industrially useful enzymes, for example, sugar isomerase (glucose isomerase): proteases: sugar and starch amylases: rennet; esterases: and oxygenases, e.g., lignin degrading enzymes and aromatic ring-cleaving enzymes. Other useful proteins which may be expressed with this system include hormones, e.g., insulin, interferons, interleukins, growth hormones, including human, bovine and chicken, and somatomedins; platelet derived growth factor tumor necrosis factor; glucagon; hypothalamic hormones (growth hormone stimulating factor, ACTH, endorphin); adrenal derived protein hormones: and rennin. In addition, this invention is of particular use in the expression of bacterial toxins and of viral proteins. These viral proteins can be used in the production of vaccines and the development of assay kits that detect the presence of either the virus or a virus-derived antibody in a biological fluid. The bacterial toxin expressed by this system can be used for the treatment of disease or for the control of pests in the environment. All of the proteins discussed above can be produced by the techniques discussed above and by other techniques that are known to persons skilled in the art.

Before detailing the construction and identity of the novel plasmids and expression system of the subject invention, there are disclosed the materials and methods employed.

(1) Media

Cultures were grown in YT medium (8 gm tryptone, 5 gm yeast extract, 5 gm NaCl per liter). Ampicillin was added to 50 μg/ml and tetracycline to 20 μg/ml as required. Glucuronidase screening plates contained 5 μg/ml β-methyl-umbelliferyl-glucuronide (MUG) as described by Dahlen and Linde ([1973] Appl. Microbiol. 26:863–866).

(2) E. coli DNA

E. coli DNA was prepared from strain MS371 essentially according to Marmur (1961, J. Mol. Biol. 3: 208–218) with modifications of Anilionis and Riley (1980, J. Bacteriol. 143:355–365.) All E. coli strains disclosed herein are E. coli K-12 derivatives.

(3) β-D-glucuronidase assays

Hydrolysis of p-nitrophenol-8-glucuronide (pNPGA) and liberation of free p-nitrophenol was measured by absorbance increase at 400 nm. Assays were calibrated with standard E. coli type VII enzyme stocks obtained from Sigma Chemical (St. Louis, Mo.). The Sigma unit definition of β-D-glucuronidase (the modified Fishman unit) is the activity that will liberate 1.0 μg phenolphthalein from phenolphthalein glucuronide in one hour at 37° C. at the optimum pH (6.8 for the E. coli enzyme). The assay procedure was as follows: Each assay tube contained 0.98 ml 50 mM $NaH_2PO_4$ (pH 6.8) pre-equilibrated with the enzyme sample or 10 units of E. coli type VII enzyme standard in 0.01 ml for 10 min at 37° C. The reactions were started by adding 0.1 ml 10 mg/ml pNPGA substrate solution, quickly mixed, and incubated at 37° C. in a water bath. Reactions were stopped by the addition of 0.1 ml 1.0N NaOH. The absorbance at 400 nm was measured against a blank containing all components except enzyme incubated for the same period at 37° C. Duplicate assays were performed for each of three different times to obtain accurate activity data.

(4) Two-dimensional gel electrophoresis

Lysates of E. coli were prepared by treatment with lysozyme followed by several freeze-thaws. Clarified supernates of these lysates were assayed for protein. These samples were then brought to 2% NP40 and 5% β-mercaptoethanol and loaded onto an isoelectric focusing gel.

The isoelectric gels were cast in acid-washed 160×2.5 mm (ID) glass tubes. Formulation of the gel solution was as follows (for 10 ml):

5.5 g urea (ultrapure, Schwarz/Mann, Spring Valley, N.Y
1.33 ml acrylamide solution (28.4% w/v acrylamide 1.6% w/v methylene bisacrylamide)
2.0 ml 10% v/v NP40
1.97 ml $H_0O$
0.60 ml ampholytes (LKB, Gaithersburg, Md.), pH 3-10
0.008 ml tetraethyl methylene diamine Following degassing of the solution, 10 μl of a 10% w/v solution of ammonium persulfate was added and approximately 1.2 ml was added to each glass tube via a 4 in or greater spinal-tap needle. The bottoms of the tubes were previously sealed with parafilm. The top of the gel was overlaid with 20 μl of deionized water and polymerization occurred within 30 min at room temperature. The isoelectric focusing gels were placed in a tube gel electrophoresis apparatus (Hoefer Scientific Instruments, San Francisco, Calif.). The lower (anodic) electrode buffer was 10 mM phosphoric acid and the upper (cathodic) electrode solution was 20 mM NaOH. The NaOH solution was freshly made or stored under vacuum to prevent $CO_2$ buildup The gels were prefocused at 300 v for 30 min prior to sample loading.

The samples (usually 100 μg protein) were layered onto the top (cathodic end) of the isoelectric focusing (IEF) gel. IEF was then carried out for 14 hr at 300 v and 2–3 hr at 800 v. The gels were extruded from the tubes and equilibrated for 30 min with a solution comprising 2.3% SDS, 62.5 mM Tris-HCl (pH 6.8), and 5% β-mercaptoethanol. The equilibrated gels were laid on top of the stacking gel of a conventional discontinuous SDS-polyacrylamide slab gel and sealed in place with a hot 1% agarose solution made up in equilibration buffer (2.3% SDS, 62.5 mM Tris-HCl (pH 6.8), 5% β-mercaptoethanol) also containing 0.01% bromophenol blue as a tracking dye.

The gels were run in the second dimension at 25 mamp/gel until the tracking dye reached the end of the gel. The slab gels were then stained with 0.24% Coomassie blue R in 50% methanol, 10% acetic acid for about 30 min at room temperature with gentle agitation. Destaining was achieved overnight in 10% methanol, 5% acetic acid, also with gentle agitation, and stained gels were then photographed directly.

(5) Plasmid DNA preparation

Procedure used for large scale preparation of plasmid DNA was essentially as follows: A 250 ml culture was grown to Log phase, amplified with chloramphenicol at O.D. 0.6 to 0.7 (or alternatively with no chloramphenicol addition) and grown overnight. Cells were pelleted at 6K, 20 min, JA14 rotor, and resuspended in 6 ml glucose buffer (50 mM glucose, 25 mM tris, 10 mM EDTA). Cells were incubated 10 min at room temp in the presence of 1 ml of 20 mg/ml lysozym,a freshly made; placed on ice with the addition of 13.8 ml 1% SDS in 0.2N NaOH for 5 min, and kept on ice an additional 15 min with 7 ml 5M KAC (pH 5.0–5.5). Debris was pelleted at 10K for 10 min and supernate extracted once with an equal volume of pheno-chloroform-isoamyl alcohol (25:24:1, TE saturated, 0.1% 8-hydroxyquinoline). Following precipitation with 0.6 vol. isopropyl alcohol, DNA was purified over CsCl gradients.

(6) Restriction enzyme digestion and isolation of desired fragments

Digestions were carried out according to suppliers-'instructions. Separation of fragments was achieved by agarose gel electrophoresis in TBE buffer (90 mM Tris, 0.89 M borate, 2 mM EDTA) containing 0.5 μg ethidium bromide/ml. Isolation of the desired fragment was achieved by excision of the appropriate region of the gel and subsequent electroelution of the DNA in 1X TBE, at 100 volts for 2 hr followed by a reversal of current for 1 min to decrease adherence of the DNA to the dialysis tubing. Eluted DNA was purified and concentrated by passing over Elu-tip columns (Schleicher and Schuell, Keene, N.H.) according to supplier's instructions, followed by precipitation in 2.5 volumes EtOH with added carrier tRNA.

(7) DNA ligations

T4 ligase was used for standard vector/insert ligations and was present in excess (200 u/μg DNA): insert was present in a 5-fold molar excess with 0.02 pmoles of vector and 0.1 pmoles of insert in a 20 μl reaction volume.

(8) Transformation

Fresh overnight cultures were diluted in L-broth and allowed to grow at 37° C. with agitation until an $A_{600}$ of 0.3 was obtained. The cells were chilled on ice, then collected by centrifugation (10 min at 4100xg). The cells were resuspended in ½ the original volume of ice cold 50 mM $CaCl_2$ and incubated on ice for 20 min. The cells were again collected by centrifugation as above and resuspended in ice cold 50 mM $CaCl_2$ (1/25 the original volume). 0.1 ml of the cell suspension was mixed with 1–10 μl (50-100 ng) of DNA plasmid solution and allowed to sit for 30 min at 0° C. The cells were then heated to 37° C. for 2 min and plated on L-broth plates containing 1.5% agar and either 10 μg/ml tetracycline or 50 μg/ml ampicillin. The plates were incubated overnight at 37° C. Transformation efficiencies of $1 \times 10^6$ colonies per μg plasmid DNA were routinely observed.

(9) Agarose electrophoresis

DNA fragments were isolated by gel electrophoresis in 0.8% agarose in 2X tris-borate buffer (178 mM tris, 178 mM boric acid, 5 mM $Na_2EDTA$ pH 8.4). Analytical and preparative gels were run in a horizontal gel box at 60 volts submerged in electrophoresis buffer (1X trisborate). DNA bands were visualized under UV light by including 5.0 μg/ml ethidium bromide (EtBr) in the gel. A slice containing the desired DNA band was cut from the gel and the DNA recovered by electrophoresis in 1X tris-borate buffer in a dialysis tube (½ in. diameter) containing 0.5–1.0 ml of buffer. Electrophoresis was carried out for 30 min at 10 volts or until the stained material was located against the side of the dialysis tubing. The gel slice was removed from the dialysis bag and the DNA recovered by repeatedly flushing the bag with tris-borate buffer. NaCl was added to the DNA solution to a final concentration of 1M and the ethidium bromide and agarose gel impurities were removed by two extractions with phenol saturated with tris borate buffer. The phenol was removed by two extractions with ether and the purified DNA was recovered by precipitation with 1/10 volume 3 M sodium acetate, pH 4.5 and 2.5 volumes cold ethanol. The precipitation reaction was carried out at −70° C. for 15–20 min. The precipitated DNA was recovered by centrifugation at 10,000 xg for 15 min. Yield of recovered fragment was assayed by direct comparison of ethidium bromide fluorescence with pure DNA standards. Typically, 50% recoveries were obtained with the yield decreasing as fragment size increased.

(10) Polyacrylamide gel electrophoresis

All SDS gels were run by the method of Laemmli (Laemmli, U.K. [1970] Nature [London] 227:680–685). These gels contained a total acrylamide concentration of 9%. Slab gels were 1.5 mm wide, run in an electrophoretic apparatus obtained from Hoefer Scientific Instruments (San Francisco, Calif.). Tube gels were run in 6 mm i.d. × 10 cm glass tubes without a stacking gel. Tube gels were stained by the following method: Gels were stirred overnight in 650 ml isopropyl alcohol, 250 ml $H_2O$, and 100 ml acetic acid, containing 1.0 g/l Coomassie blue. Then they were stirred overnight again in 100 ml acetic acid, 100 ml isopropyl alcohol, and 800 ml $H_2O$, containing 0.05 Coomassie blue. A third overnight stirring was done in 10% acetic acid. The gels were then scanned using a Beckman model 34 spectrophotometer equipped with a model 576767 gel scanner (Beckman Instruments). Percent expression was determined by cutting out the protein peaks and weighing the paper. Percent hybrid protein expression is calculated as [weight of β-glucuronidase protein/weight of total protein peaks] × 100%.

(11) Bacterial strains and media

The source and genotype of all bacterial strains used are listed infra. All strains were maintained and grown using YT medium (8 gm/l tryptone, 5 gm/l yeast extract, and 5 gm/l sodium chloride).

(12) Chemicals

Growth media components were obtained from Difco (Detriot, Mich.). Acrylamide was obtained from Accurate Chemical & Scientific Corp., (Westbury, N.Y.). All other chemicals were obtained from Sigma Chemical Co. (St. Louis, Mo.).

(13) Cultures (All *E. coli* K-12 strains)

| (A) | Bacterial Strains | Relevant Genotype | Repository Number |
|---|---|---|---|
| | *E. coli* MS371 | F−, Gal−, Thi−, endA, sbcB, hsdR4 | NRRL B-15129 Deposited Aug. 18, 1982 and now available to the public. |
| | *E. coli* GMS407 | argE3, lacY1, galK2, man4, uidA1, mtl1 | NRRL B-15917 Deposited on Dec. 7, 1984. |
| | *E. coli* HB101 | Pro−, Leu−, Thi−, lacY, hsdR, endA, recA, rpsL20, supE44 | NRRL B-11371 Available to the public |

(B) Bacterial Host

| Containing Plasmid | Repository Number |
|---|---|
| MS371(pBG101-41) | NRRL B-15905 Deposited Nov. 1, 1984 |
| MS371(pBG1) | NRRL B-15904 Deposited Nov. 1, 1984 |

(C) Plasmid

Plasmid pBR322 is a well-known and available plasmid. It is maintained in the *E. coli* host ATCC 37017. Purified pBR322 DNA can be obtained as described in Bolivar, F., Rodriquez, R. L., Greene, P. J., Betlach, M. C., Heyneker, H. L., Boyer, H. W., Crosa, J. H. and Falkow, S. (1977) Gene 2:95–113; and Sutcliffe, J. G. (1978) Nucleic Acids Res. 5:2721–2728.

NRRL B-15905, NRRL B-15904, and NRRL B-15917 are available to the public upon the grant of a patent which discloses these accession numbers. It should be understood that the availability of these deposits does not constitute a license to practice the subject invention in derogation of patent rights granted for the subject invention by governmental action. The culture deposits are in the permanent collection of the Northern Regional Research Laboratory (NRRL), U.S. Department of Agriculture, Peoria, Ill., U.S.A.

There are other well-known *E. coli* hosts which can be used instead of *E. coli* MS371, for example, E. coli RRl, HB101, and *E. coli* GMS407 (Novel, M. and Novel, G. [1973] Mol. Gen. Genet. 120:319).

Further, other prokaryotic hosts which can be used are microbes from the genera Salmonella, Pseudomonas, Bacillus, Streptomyces, and the like.

(14) Isolation of recombinant plasmid DNA from transformed host

Recombinant plasmid DNA can be isolated from its prokaryotic host by well-known procedures, e.g., using cleared lysate-isopycnic density gradient procedures, and the like.

(15) DNA sequencing

DNA sequence determination was carried out as described by Maxam and Gilbert (1977, Proc. Natl. Acad. Sci. U.S.A. 74:560–564) and Sanger, F. Nicklen, S. and Coulson, A. R. (1977) Proc. Natl. Acad. Sci. USA 74: 5463–5467.

It is within the skill of those in the art to vary the conditions required to grow cells, extract DNA, perform restriction enzyme digestions, electrophorese DNA fragments, tail and anneal plasmid and insert DNA, ligate DNA, transform cells, prepare plasmid DNA, electrophorese proteins, and sequence DNA.

(16) Construction of hybrid plasmids

The source for the $\beta$-glucuronidase (BG) gene DNA used to construct hybrid plasmid pBG101-41 was *E. coli* MS371. This BG gene DNA was inserted into the BamHI site of pBR322. Ligation mixtures were transformed into competent cells of *E. coli* which lack BG activity. Subsequent plating on YT agar, followed by screening and purification yield a clone designated BG101-41. Plasmid DNA was isolated from this clone and retransformed. The identity of plasmid pBG101-41 was then established by size of DNA, restriction endonuclease pattern and expression of BG in prokaryotic host.

Novel hybrid plasmid pBG1 was constructed from plasmid pBG101-41 by taking the 1237 bp SalI-BamHI fragment of pBG101-41 and ligating it into a SalI, BamHI cut pBR322 vector. The identity of pBG1 was established as above for pBG101-41.

Following are examples which illustrate procedures, including the best mode, for practicing the invention. These examples should not be construed as limiting. All percentages are by weight and all solvent mixture proportions are by volume unless otherwise noted.

Example 1—Construction of Hybrid Plasmid pBG101-41

Twenty $\mu$g of *E. coli* MS371 DNA was incubated at 37° C. with 2 units Sau3A enzyme in a reaction volume of 200 $\mu$l; 50 $\mu$l aliquots were removed and the reaction terminated by heating to 80° C. after 2 min, 5 min, 10 min, and 30 min. Examination of 1 $\mu$g samples after gel electrophoresis through 1% agarose showed that the 2 min and 5 min samples contained partial digests with average molecular lengths in the 5–10 kb range. One microgram amounts of each of these partial digests were ligated with 0.2 $\mu$g BamHI cleaved pBR322 which had also been heat-treated to inactivate the restriction enzyme. Ligation mixtures were transformed into competent cells of the *E. coli* mutant strain GMS407 (NRRL B-15917) which lacks $\beta$-glucuronidase activity and each mixture spread over 10 YT agar plates supplemented with 50 $\mu$g/ml ampicillin and 5 $\mu$g/ml MUG. After overnight incubation at 37° C., the plates were examined under ultraviolet light. Each plate was densely covered with colonies but on three plates a single focus of intense fluorescence was seen. Colonies from these foci were purified by restreaking on YT, ampicillin, MUG agar plates. After four rounds of purification yielding isolated intensely fluorescent colonies, one such purified clone, designated BG101-41, was chosen for further study. Isolation of plasmid DNA from this transformation and retransformation into *E. coli* strains GMS407, MS371, and HB101 showed that the MUG+fluorescence phenotype was coselected with ampicillin resistance conferred by the plasmid pBG101-41.

Figure 1:
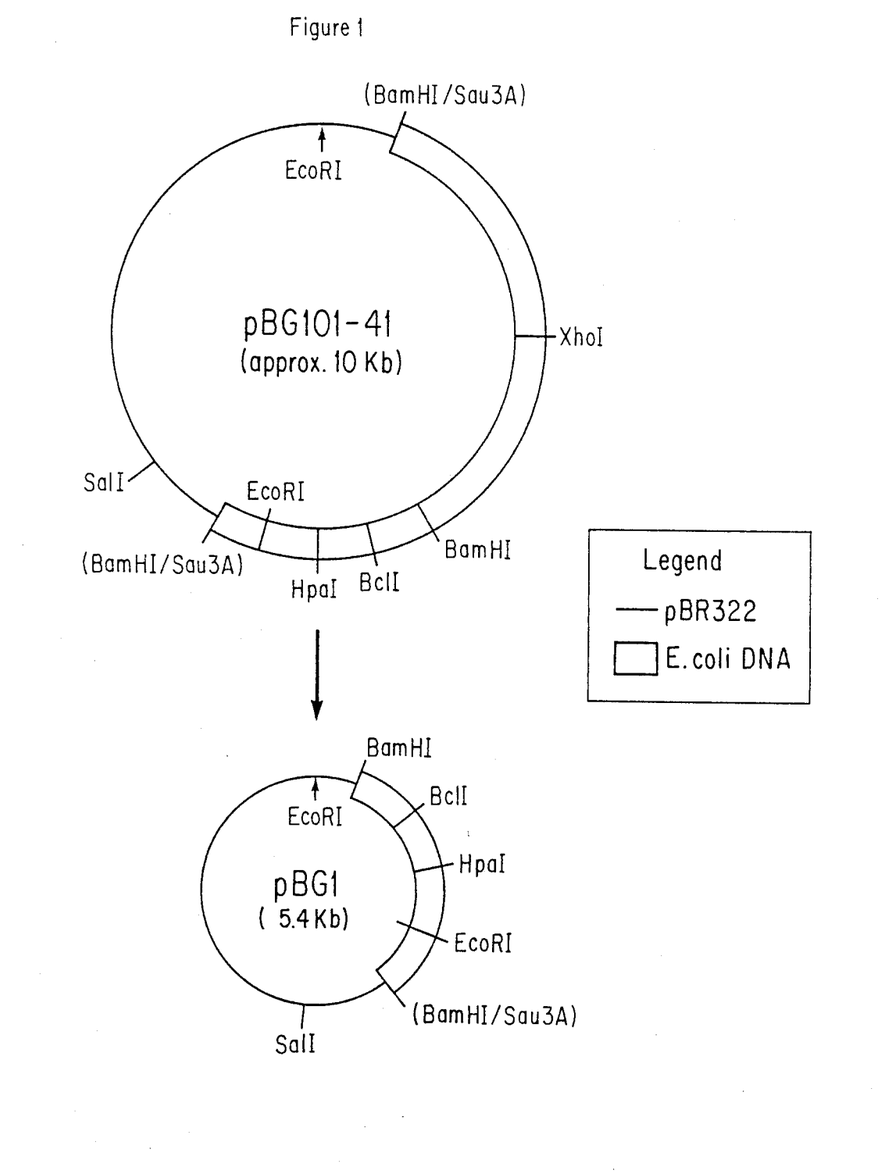
FIG. 1 depicts the endonuclease restriction map of plasmids pBG101-41 and pBGl.

A restriction site map of pBG101-41 plasmid DNA was derived and is presented in FIG. 1. The *E. coli* DNA insert was determined to be approximately 6 kb in extent and contain single recognition sites for the endonucleases BamHI, EcoRI, and XhoI. The insert was not cut by PstI, ClaI, HindIII, or SalI.

The presence of high levels of $\beta$-glucuronidase activity in pBG101-41 transformed strains was confirmed by the pNPGA assay. Lysozyme-EDTA lysed GMS407(pBG101-41) and MS371 (pBG101-41) cells showed similar activities of 1,000-1,500 units $\beta$-D-glucuronidase activity/mg wet weight cells. 100 $\mu$g protein samples of clarified lysates of YT grown stationary phase cultures of MS371 and MS371(pBG101-41) were resolved by two-dimensional electrophoresis as described previously. The pattern of proteins seen in the MS371 lysate is that of a typical *E. coli* strain, whereas the MS371(pBG101-41) lysate exhibits a single major protein species with a much diminished content of the normal complement of *E. coli* proteins. This major protein has an apparent molecular weight of 72Kd and an isoelectric point of approximately 6.8, consistent with the properties of *E. coli* $\beta$-glucuronidase enzyme. The major protein is clearly more abundant than any other protein in the cell and visual estimates suggest that it may in fact constitute over 50% of the total cellular protein. This corresponds to a level of over 6% of the wet weight of the cells.

Glucuronidase enzymes from other sources exist in tetrameric form leading to the prediction that the native *E. coli* enzyme should have a very high molecular weight and might be separated from other host proteins by gel filtration. Nine ml of crude lysate of MS371(pBG101-41) cells containing $3.5 \times 10^6$ units of $\beta$-D-glucuronidase activity were mixed with 1.5 ml 0.5M sodium phosphate pH 6.8 and loaded onto an Ultragel ™ ACA34 (LKB, Gaithersburg, Md.) column (2.5 cm $\times$ 120 cm, 590 ml capacity) at a flowrate of 1 ml/min. The column was run in 50 mM sodium phosphate pH 6.8, 1mM EDTA, 1 mM DTT. A single peak of partially included protein was $\beta$-glucuronidase activity eluted from the column well before the low molecular weight protein peak. The $\beta$-glucuronidase peak recovered showed a total activity of $2.1 \times 10^7$ units (a six-fold increase over the total apparent activity of the column load) and a protein content of 490 mg. The increase in apparent activity may be due to removal of inhibitory agents in the crude lysate from the enzyme preparation. The specific activity of this fraction was therefore $4.2 \times 10^7$ $\mu$/gm. Samples (20 $\mu$g) of four such purified enzyme preparations run on a 12% polyacrylamide gel were judged to be greater than 95% pure β-D-glucuronidase after only one column purification step.

Example 2--Construction of Hybrid Plasmid pBG1

Hybrid plasmid pBG1 was constructed as shown in FIG. 1. pBG1 is a clone of the 1237 bp SalI-BamHI fragment of pBG101-41 ligated into a SalI, BamHI cut pBR322 vector. This plasmid was transformed into MS371 and GMS407 and the total protein content of overnight cultures of these transformants were examined on SDSpolyacrylamide gels. Four isolates of MS371(pBG1) showed the presence of an abundant protein of approximately 20Kd molecular weight which is not found in the MS371 parent. This protein is presumed to be the truncated uidA enzyme terminated after the BamHI site in pBG1, and accumulates to an estimated 15% of the total cellular protein, producing a 20Kd truncated N-terminal fragment of the enzyme which has no β-glucuronidase activity. This corresponds to a similar number of molecules expressed per cell as for the clone BG101-41, since the truncated polypeptide is of the order of one quarter the size of the intact enzyme. The plasmid pBG1 thus carries all the sequences necessary to specify the high level expression observed in clone BG101-41.

In order to check for the presence of an uidR operator site in pBG1 strains, GMS407(pBG1) and MS371(pBG1) were examined on plates containing β-methyl-umbelliferyl-glucuronide (MUG). Fluorogenic activity was present in the MS371 strain but not in GMS407. Since the activity is not seen in the GMS407 host, it cannot be directly contributed by the plasmid, and since the activity appears in MS371(pBG1) the phenomenon must be due to derepression of the chromosomal uidA gene copy. Thus the plasmid pBG1 copies carry uid operator sites which bind the repressor molecules releasing repression of the host uidA gene.

Figure 2:
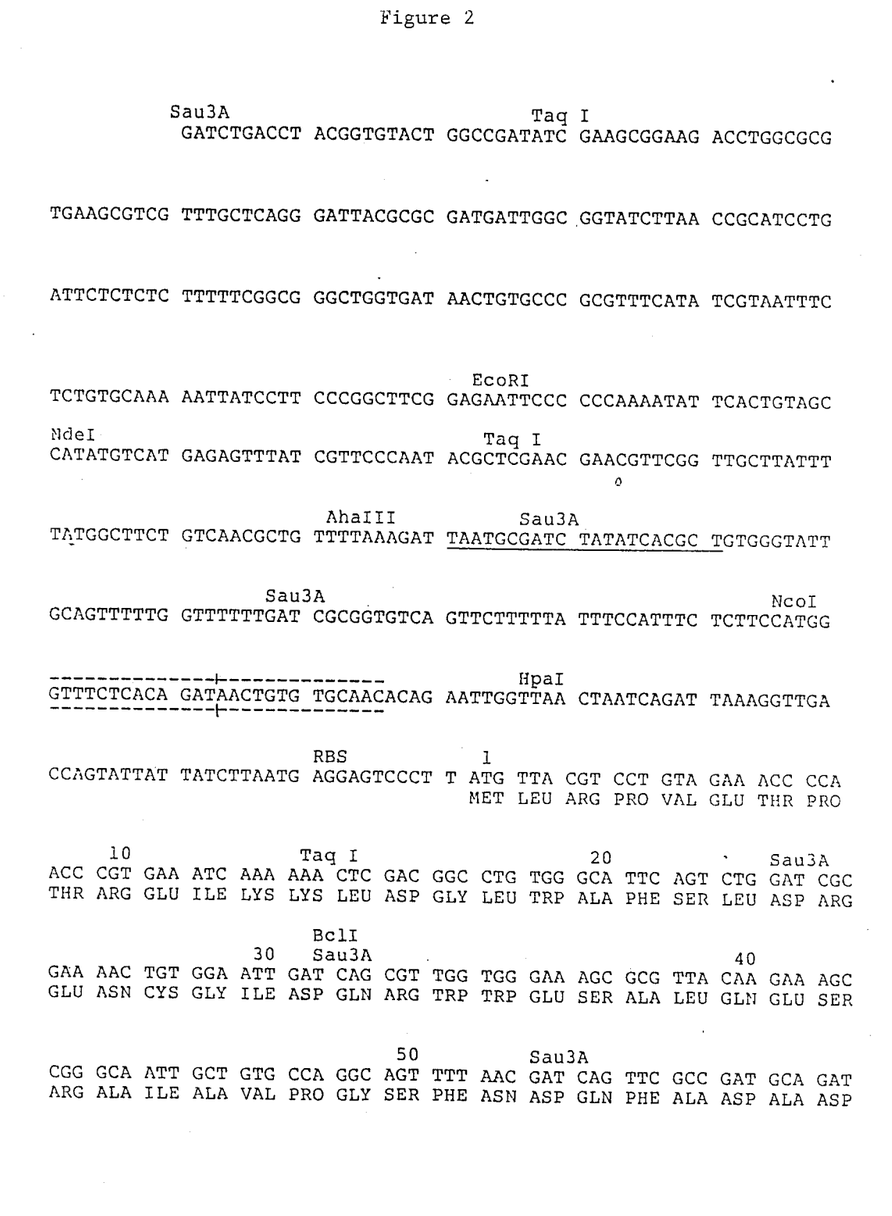
FIG. 2 depicts the *E. coli* BG insert DNA sequence of pBGl. The 26 bp dyad is outlined by dashed lines. RBS=ribosome binding site.

FIG. 2 shows the E. coli BG insert DNA sequence of BG1. The single open reading frame truncated at the BamHI site is the uidA structural gene. The nucleic acid sequence of the upstream control region is disclosed, along with the adjoining 170 codons of the N-terminal segment of the structural gene. The 17 N-terminal amino acid residues of the β-D-glucuronidase enzyme have been confirmed by amino acid sequencing of the isolated protein product.

Computer-aided searches of the DNA sequence of the uidA gene upstream control region reveal a potential promoter configuration, a presumptive CAP-binding site, a 26 bp imperfect dyad symmetry which may be involved in repressor binding, and a strong ribosome binding site with an appropriately spaced methionyl initiator codon.

Since plasmid pBG1 carries all the sequences necessary for high expression, it can be used as a transfer vector for the expression of useful proteins, as discussed previously. The procedures for use of the nucleotide sequence of pBG1 shown in FIG. 2 to function as a promoter sequence in a variety of transfer vectors and prokaryotic hosts are well known and standard in the art. For example, the promoter DNA sequence of Chart A can be used in much the same manner as the lac promoter is presently used in the art. Further, it has been determined that only a portion of the nucleotide sequence shown in FIG. 2 can be used as a promoter to produce a very high level expression (over 50% of total cellular protein of a useful protein (protein A) in a prokaryotic (E. coli) expression system. We have shown that the following sequence confers extremely high expression activity:

```
NdeI                                          Taq I
CATATGTCAT  GAGAGTTTAT  CGTTCCCAAT  ACGCTCGAAC

GAACGTTCGG  TTGCTTATTT  TATGGCTTCT  GTCAACGCTG

AhaIII                  Sau3A
TTTTAAAGAT  TAATGCGATC  TATATCACGC  TGTGGGTATT

Sau3A
GCAGTTTTTG  GTTTTTTGAT  CGCGGTGTCA  GTTCTTTTTA

NcoI
TTTCCATTTC  TCTTCCATGG  GTTTCTCACA  GATAACTGTG

HpaI
TCCAACACAG  AATTGGTTAA  CTAATCAGAT  TAAAGGTTGA

RBS
CCAGTATTAT  TATCTTAATG  AGGAGTCCCT  T  ATG  TTA  CGT

Taq I
CCT  GTA  GAA  ACC  CCA  ACC  CGT  GAA  ATC  AAA  AAA  CTC

GAC  GGC
```

The above nucleotide sequence can be readily engineered by a person skilled in the art so that any part of the sequence can be used in an expression system to enhance the production of useful proteins. For example, the sequence can be cut at any one of the restriction sites shown, and at others not shown, to give a variety of segments of the sequence. Further, once the sequence is cut with one or more restriction endonucleases, the resulting fragments can be "chewed back" further by use of exonucleases: or synthetic linkers can be added. In addition a double-stranded synthetic oligonucleotide fragment incorporating a multiple cloning site comprising several restriction endonuclease recognition sequences could be inserted into the translated region and the cloned segment would then have a more general utility. These operations all can be done by a person skilled in the art without undue experimentation. Thus, the scope of the subject pioneer invention encompasses all or part of the nucleotide sequence shown above, provided that which is used enhances the level of expression in the prokaryotic expression system employed. Again, whether there is an enhancement of the expression level in a prokaryotic expression system can be readily ascertained by a person skilled in the art, using standard procedures described herein, without undue experimentation.

It should also be clear that the scope of the subject invention includes use of all or part of the disclosed BG structural gene sequence and all or part of the upstream untranslated DNA sequence of the BG promoter region not only to produce BG but also as part of an expression system to produce other useful proteins, many of which are exemplified herein. In using the subject invention thusly, a person skilled in the art could readily determine whether all or only a part of the BG promoter and gene DNA would function best to give the high expression levels of desired protein. This determination, which can be done without undue experimentation, may well show that part or all of the 271 base pairs of the upstream untranslated sequence disclosed above, along with all or part of the first 17 codons of the BG structural gene shown in FIG. 2 and reproduced above, would give the highest expression level in a particular expression system designed for the production of a specific useful protein.

It should be readily evident to a person skilled in the art that the proteins produced by the BG expression system of the subject invention may be hybrid proteins, in that DNA from the expression system would be transcribed along with the particular protein gene DNA. These hybrid proteins would still retain the primary function(s) of the desired protein and, thus, could be used as the desired protein is used. If preferred, it is well within the skill of those in the art to further process the hybrid protein and recover the desired protein.

As is well known in the art, the nucleic acid sequence upstream of the structural gene specifies its promoter. Only certain of these nucleotides are important for promoter activity: those located 35 bases upstream, and those located 10 bases upstream of the site at which the mRNA is initiated. See, for example, Hawley, D. K. and McClure, W. R. (1983) Nucl. Acids Res. 11:2237–2255. The CAP protein (catabolite activator protein) is known to bind at certain promoter sites and to stimulate expression from that promoter: DeCrombrugghe, B., Busby, S. and Buc, H. (1984) Science 224:831–838. Nucleotide sequences interspersed between these sites may not contribute to expression activity. Thus certain bases can be changed without affecting this activity. Also, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATH | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Try) | TGG |
| Alanine (Ala) | GCL | Arginine (Arg) | WGZ |
| Tyrosine (Tyr) | TAK | Glycine (Gly) | GGL |
| Termination signal | TAJ | | |
| Termination signal | TGA | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence. A =adenine G =guanine C =cytosine T =thymine X =T or C if Y is A or G X =C if Y is C or T Y =A, G, C or T if X is C Y =A or G if X is T W =C or A if Z is A or G W =C if Z is C or T Z =A, G, C or T if W is C Z =A or G if W is A QR =TC if S is A, G, C or T J =A or G K =T or C L =A, T, C or G M =A, C or T The above shows that a novel amino acid sequence can be prepared by more than one nucleotide sequence. Accordingly, the subject invention includes such equivalent nucleotide sequences.

The work described herein was all done in conformity with physical and biological containment requirements specified in the NIH Guidelines.

We claim:

1. A hybrid protein prepared by a process which comprises culturing a Gram negative prokaryotic host expressing a DNA segment on a transfer vector, wherein said DNA segment comprises the promoter region of the β-glucuronidase gene of E. coli and wherein said promoter region is operably attached to a first DNA sequence encoding 17 or more amino acids of the N-terminus of the β-glucuronidase gene and wherein said first DNA sequence is fused to a second DNA sequence encoding an amino acid sequence foreign to E. coli and wherein said promoter is functional in said host directing the expression of said hybrid protein.

* * * * *

UNITED STATES PATENT AND TRADEMARK OFFICE
CERTIFICATE OF CORRECTION

PATENT NO.    :   4,952,682

DATED         :   August 28, 1990

INVENTOR(S)   :   Algis Anilionis, John L. Palmer

It is certified that error appears in the above-identified patent and that said Letters Patent is hereby corrected as shown below:

Column 1: line 5: "no abandoned" should read --now abandoned--; line 36: "oroduces" should read --produces--.

Column 2: line 14: "SalI. BamHI" should read --SalI, BamHI--; line 18: "2" should read --2.--; line 37: "enz)nne" should read --enzyme--; line 67: "factor tumor" should read --factor; tumor--.

Column 3: line 25: "E. coli" should read --*E. coli*--; line 30: "E. coli" should read *E. coli*--; line 32: "p-nitrophenol-8-glucuronide" should read --p-nitrophenol-$\beta$-glucuronide--.

Column 4: line 1: "$H_0O$" should read --$H_2O$--; line 50: lysozym,a" should read --lysozyme--; lines 61-62: "suppliers-'instructions" should read --suppliers' instructions--.

Column 8: line 66: "4.2 x $10^7$ $\mu$/gm" should read --4.2 x $10^7$ u/gm--.

Column 9: line 11: "SDSpolyacrylamide" should read --SDS-polyacrylamide--.

Column 10: lines 15-16: "Chart A" should read --Figure 2--; line 56: "exonucleases:" should read --exonucleases;--.

Signed and Sealed this

Third Day of December, 1991

Attest:

HARRY F. MANBECK, JR.

*Attesting Officer*     *Commissioner of Patents and Trademarks*